(12) United States Patent
Bjørnsen

(10) Patent No.: US 7,547,542 B2
(45) Date of Patent: Jun. 16, 2009

(54) ARRANGEMENT AND METHOD FOR A CASSETTE FOR PREPARATION OF BIOLOGICAL SPECIMENS

(75) Inventor: Bjørn G. Bjørnsen, Sandnes (NO)

(73) Assignee: Total Biopsy AS, Stavanger (NO)

( * ) Notice: Subject to any disclaimer, the term of this patent is extended or adjusted under 35 U.S.C. 154(b) by 90 days.

(21) Appl. No.: 10/492,885

(22) PCT Filed: Oct. 10, 2002

(86) PCT No.: PCT/NO02/00366

§ 371 (c)(1),
(2), (4) Date: Apr. 16, 2004

(87) PCT Pub. No.: WO03/034033

PCT Pub. Date: Apr. 24, 2003

(65) Prior Publication Data

US 2005/0100981 A1    May 12, 2005

(30) Foreign Application Priority Data

Oct. 19, 2001   (NO) ................... 20015130

(51) Int. Cl.
*C12M 1/00* (2006.01)
*B01L 3/00* (2006.01)

(52) U.S. Cl. .............. 435/307.1; 435/288.3; 435/305.4; 435/40.52; 422/99; 422/102

(58) Field of Classification Search .............. 435/307.1; 220/787–789
See application file for complete search history.

(56) References Cited

U.S. PATENT DOCUMENTS

| 2,878,848 | A | * | 3/1959 | Coltman, Jr. ................. 220/789 |
| 3,733,768 | A | | 5/1973 | Carls et al. |
| 3,982,862 | A | | 9/1976 | Pickett et al. |
| 4,569,647 | A | * | 2/1986 | McCormick ................. 425/117 |
| 4,715,545 | A | * | 12/1987 | Hanifl et al. .............. 241/169.1 |
| 4,801,553 | A | * | 1/1989 | Owen et al. ................. 436/174 |
| 5,129,517 | A | * | 7/1992 | Hustad ........................ 206/467 |
| 5,269,671 | A | * | 12/1993 | McCormick ................. 425/117 |
| 5,817,032 | A | | 10/1998 | Williamson et al. |
| 5,843,700 | A | * | 12/1998 | Kerrod et al. .............. 435/40.5 |

FOREIGN PATENT DOCUMENTS

| EP | 0807807 A1 | 11/1997 |
| EP | 0856729 A2 | 8/1998 |
| GB | 1230913 A | 5/1971 |
| GB | 2189596 A | 10/1987 |
| JP | 3-63841 | 6/1991 |

* cited by examiner

*Primary Examiner*—William H Beisner
(74) *Attorney, Agent, or Firm*—Marger Johnson & McCollom, P.C.

(57) ABSTRACT

A method and an arrangement for preparing a biological specimen (20), where the biological specimen (20), prior to being examined in e.g. a microscope, is dried, embedded in wax and optionally sliced, and where the biological specimen (20) is placed in a container (1) with a lid/clamping member (2) that is closed, in which it is retained by a biasing element (6), the specimen (20) remaining in the same closed container/lid (1, 2) during the subsequent drying and embedment operations, whereupon the container (1) is removed from the lid (2) and the specimen (20) prior to any slicing operations.

7 Claims, 7 Drawing Sheets

ARRANGEMENT AND METHOD FOR A CASSETTE FOR PREPARATION OF BIOLOGICAL SPECIMENS

This invention regards a cassette (BioCassette) for use in preparing biological specimens to be analysed in a microscope. The cassette is compatible with known laboratory equipment and allows the use of a simplified method that does not subject the specimens to the relatively large number of manipulations/repacking operations that comes with prior art.

It is customary for biological specimens that to a substantial degree are taken from humans and animals, among other things to be able to make a medical diagnosis for a number of illnesses and diseases, to be prepared in order to allow pathological examinations by use of microscope.

Obviously, it is important during this preparation process to treat the specimens in accordance with procedures which ensure that specimens are not exchanged, destroyed, contaminated or lost, and that they retain their physical and pathological properties.

Daily preparation of a large number of biological specimens involves a considerable cost for health institutions and patients.

According to prior art, one or more biological specimens, hereunder designated the specimen, are first placed in one holder, which in turn is placed in a larger container containing formalin. After the specimen arrives at the laboratory, the preparation of the specimen starts by removing it from the formalin container and placing it on a filter paper. The filter paper is folded around the specimen and placed with the specimen in a cassette adapted to the subsequent preparation operations. The cassette is closed and placed in a drying apparatus where the water in the specimen is driven out by means of solvents and pure alcohol in combination with moderate heating and pressure fluctuations.

After drying, the cassette is opened, and the filter paper is removed and opened. The specimen is transferred from the filter paper to a mould in which it is placed at the bottom of the mould. Then it is fixed to the bottom of the mould by a few drops of liquid paraffin wax. When the paraffin wax has solidified, the cassette is placed over the mould. The remaining mould volume and the cassette are filled with paraffin wax. When the paraffin wax has solidified, the mould is removed. With this, the specimen is set in a paraffin moulding projecting down from the cassette.

The cassette is then mounted in a cutting machine/slicer where thin slices of wax and specimen are sliced from the downward face of the wax moulding.

Obviously, the preparation process according to prior art is time-consuming and requires that considerable care be taken in order to avoid any mix-up of the specimens. The many part operations are time-consuming and entail a great risk of exchange, cross contamination, general contamination, physical destruction, loss of specimens and contamination of tissue.

The object of the invention is to remedy the disadvantages of prior art.

The object is achieved in accordance with the invention by the characteristics given in the description below and in the appended claims.

Upon sampling, the specimen is placed directly on the bottom of a container. The inside of the bottom may have a layer of material with the same properties as those explained below in relation to the biasing material. In this invention, the term porous material refers to a material having open pores. A deformable, preferably flexible resilient biasing material is placed over the specimen. Advantageously, the biasing material is connected to the downward facing side of a lid, where the lid is a complementary fit to the container. Hair-like bows, wool, foam or a spongy material are examples of biasing materials. Optionally, another form of pliant, resilient structure may be used. Preferably and for several reasons—see below—the materials in contact with the specimen are porous and/or such that they do not impede the free flow of preparation fluid and wax.

The lid is pressed down into the container, where it is locked to the container with sufficient force, e.g. by use of a snap lock, the biasing material pressing the specimen against the bottom of the container so as to prevent the specimen from moving during the further processing. The container, the biasing material, the specimen and the lid are immediately placed in formalin for transport or temporary storage.

In a preferred embodiment, the lid is provided with plate-like, outwardly projecting portions that in addition to fitting as a holder in known slicers, are also suited for marking of the specimen, e.g. by means of bar codes.

When the specimen arrives at the laboratory, it may be placed in a feed/drying machine without intermediate re-packing, in which machine the moisture in the specimen is removed and where the last operation includes applying a thin layer of wax. After the drying is complete, the container receives an additional fill of liquid paraffin wax through the perforations in the lid. After the paraffin wax has solidified, the container may be removed. With this, the specimen is set in a wax moulding projecting down from the lid. The lid with the sample is then placed in a slicer that is known per se, and in which thin slices are cut from the underside of the wax moulding.

Thus when using the device of the invention, the specimen is placed directly in a container with a lid that may be marked in advance, and remains in the same packing until the specimen is cut into slices. It is obvious that the savings gained in preparation time and operations, together with the increased safety against exchanges, contamination, destruction and loss of specimens, are highly favourable characteristics of the device. In this manner, the exposure of laboratory personnel to environmentally unfavourable substances is reduced, along with the requirements for special training.

The deformable materials that abut the specimen in a supporting manner must not impede the free flow of the fluids employed. By carrying out a modest modification or calibration of the processing machine, the container may be filled with a sufficient amount of wax to obviate the need for a subsequent fill-up of additional wax, such as described above. The following describes a non-limiting example of a preferred embodiment illustrated in the accompanying drawings, in which.

Figure 1:
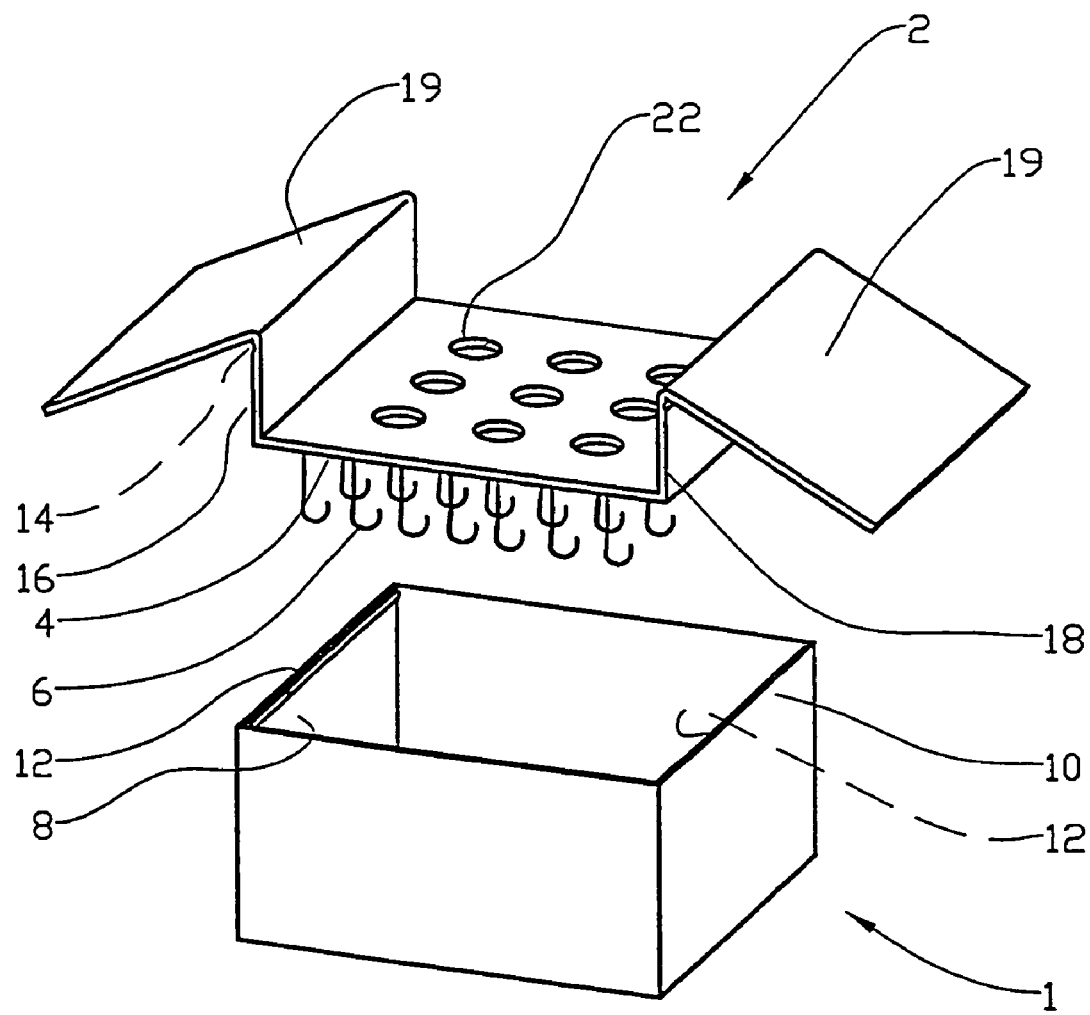
FIG. 1 is a perspective view of a container and a lid having downwardly projecting spring bows.

In the drawings, reference number 1 denotes a specimen container. A lid 2 designed to be pushed down into the specimen container 1 is provided with a biasing element 6 on the perforated side 4 facing the specimen container 1, see FIG. 1. The biasing element 6 may as an example be in the form of hair-like springs, bows, spirals, wool, foam or a spongy porous material.

Figure 3:
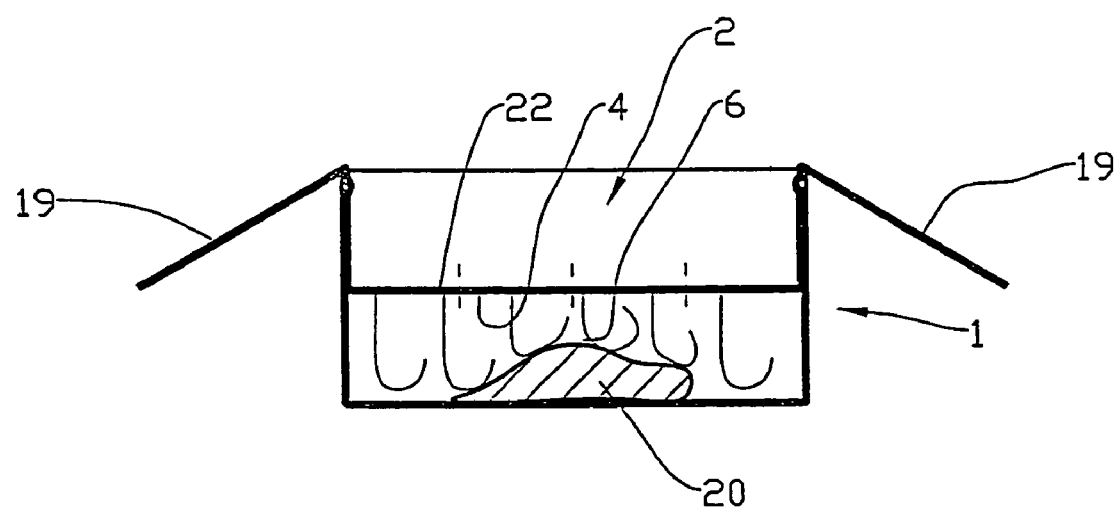
FIG. 3 shows the section I-I after the lid has been pushed down into the container and the spring bows of the lid abut the tissue sample in a clamping manner.

On the inside, along two of its opposite upper side edges 8 and 10, the specimen container 1 is equipped with inwardly projecting beads 12 that are designed to fit lockingly in two complementary grooves 14 in the vertical side faces 16 and 18 of the lid 2 upon the lid 2 being pushed into the specimen container 1, see FIG. 3. The lid 2 has at least one outwardly projecting plate 19 well suited for marking of the specimen.

Figure 2:
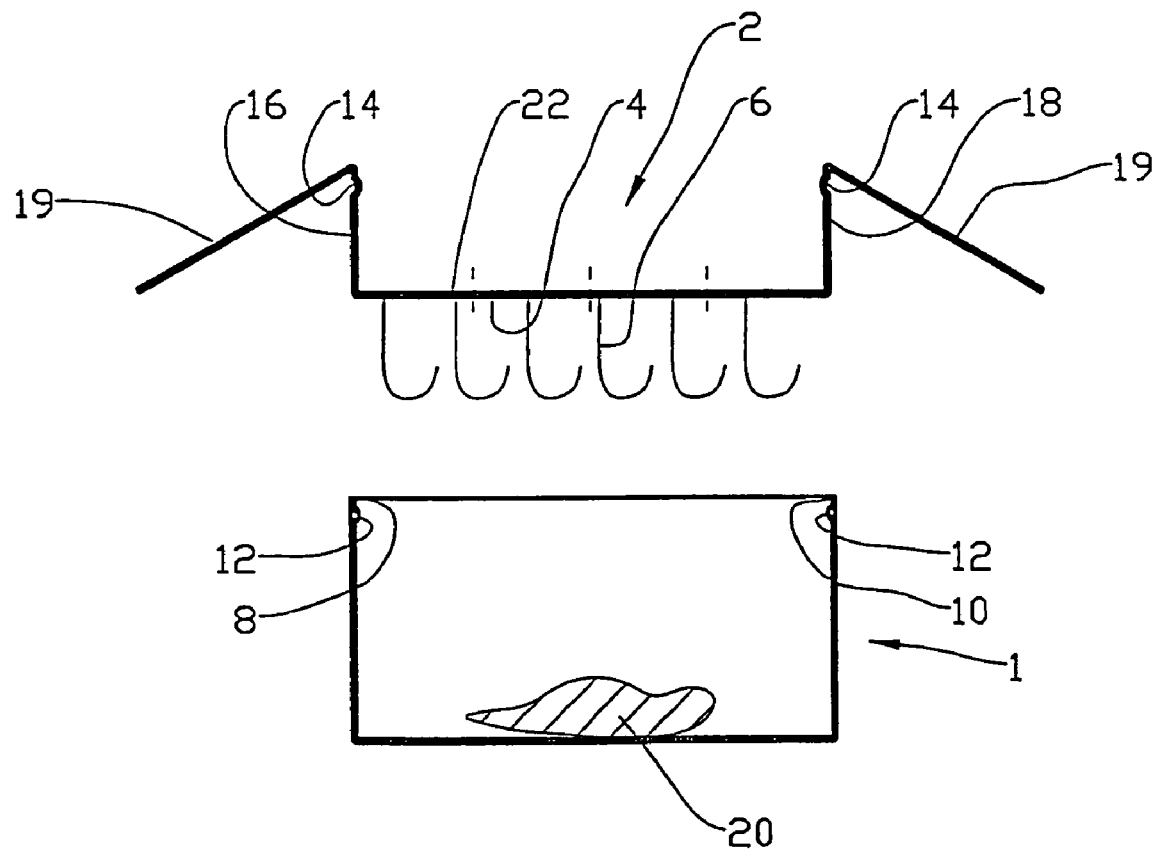
FIG. 2 is a section I-I through the container and the lid after a biological tissue sample has been placed in the container, but before the lid is pushed down into the container.

When taking a biological specimen 20, it is immediately placed in the specimen container 1, see FIG. 2. Then the lid 2, which may be marked in advance, is pushed down into the specimen container 1 until the beads 12 of the container 1 correspond with and are pushed into the grooves 14 of the lid 2, see FIG. 3. The biasing element 6 of the lid abuts the specimen 20 in a clamping manner, pressing it against the bottom of the specimen container 1.

Figure 4:
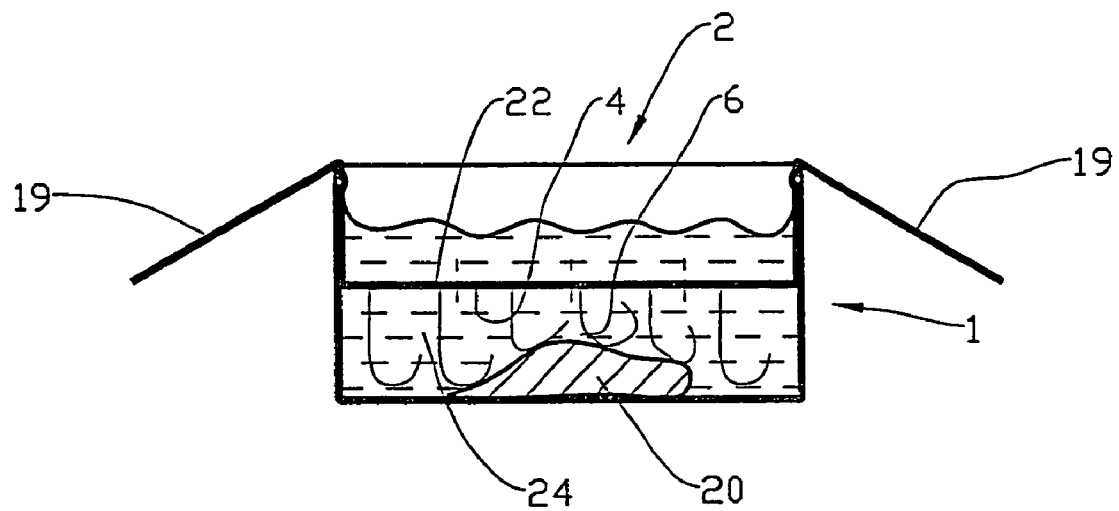
FIG. 4 shows the section I-I after the container and the lid have been filled with wax.

After the specimen has been dried, the specimen container 1 and the lid 2 are filled with liquid wax 24, see FIG. 4. The specimen container 1 is filled through the perforations 22 in the lid 2.

Figure 5:
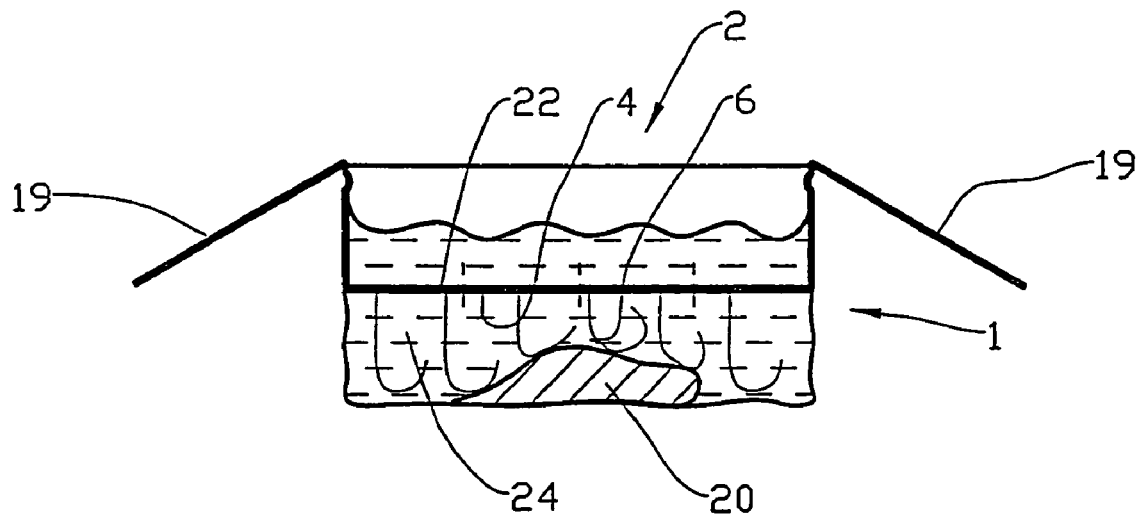
FIG. 5 shows the section I-I after the container has been removed.

The specimen container 1 is removed after the wax 24 has solidified, see FIG. 5, whereby the specimen is ready to be sliced.

Figure 6:
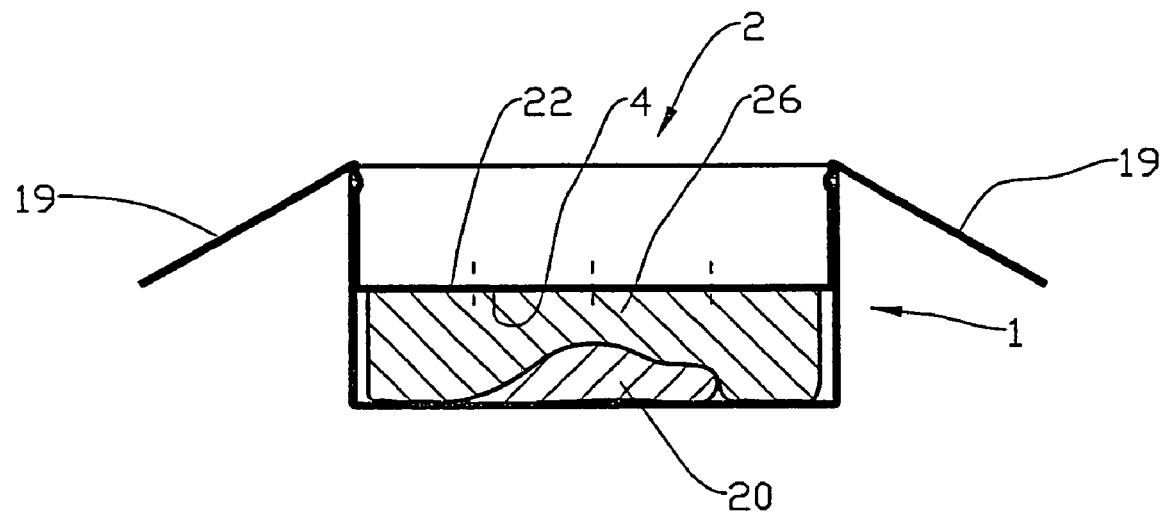
FIG. 6 shows a section where the resilient element of the lid is constituted by a spongy material.

In an alternative embodiment, see FIG. 6, the resilient element may be constituted by a spongy porous body 26 designed to be filled with wax.

Figure 7:
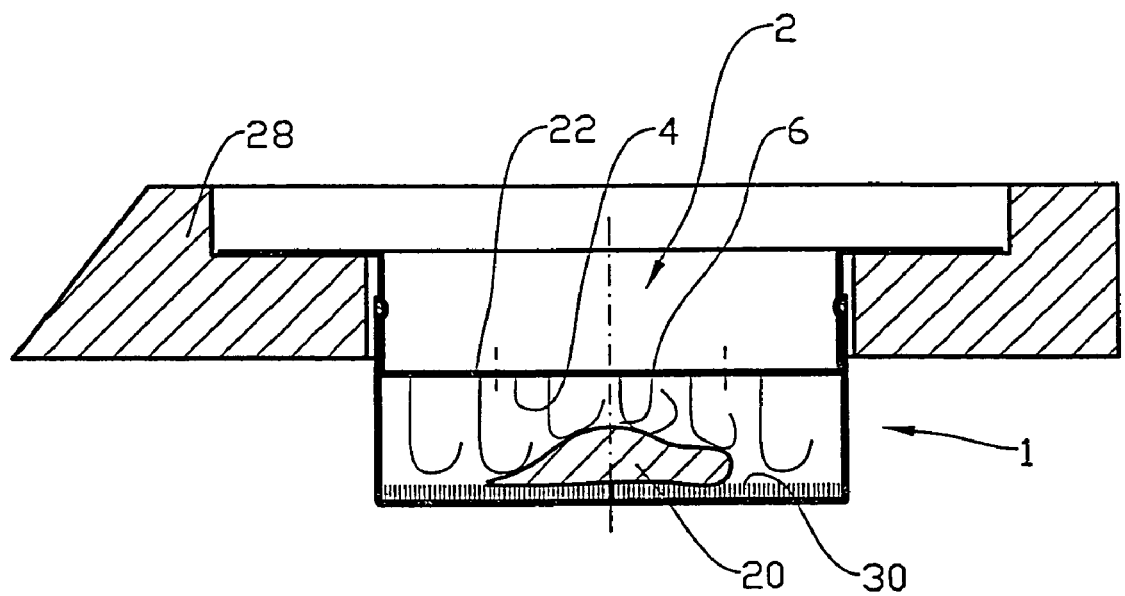
FIG. 7 shows a section through an alternative embodiment of the device according to the invention.

In a further alternative embodiment, see FIG. 7, the container 1 and the lid 2 are cylindrical and placed in a separate holder 28, where the holder 28 serves as a holder in the slicer. A porous material 30, which may also be deformable, is arranged underneath the specimen 20.

The invention claimed is:

1. A biological specimen container, comprising:
a container body having side walls, a bottom, and an inner bottom surface, where at least one of the container side walls includes a projected bead;
a container lid having an inner lid surface, the container lid including at least one groove corresponding to the projected bead such that the container lid is structured to lock to the specimen container; and
a plurality of biasing elements coupled to the inner lid surface of the lid and configured to apply a retaining force to a biological specimen toward the inner bottom surface of the container body when the lid is fitted to the container body, each of the plurality of biasing elements including a hair-like spring having a first end attached to the inner lid surface of the lid, wherein each biasing element extends substantially perpendicularly from the inner lid surface to a second end.

2. The biological specimen container of claim 1, wherein the plurality of biasing elements are spaced apart from each other.

3. The biological specimen container of claim 2, wherein the plurality of biasing elements are spaced apart to cover substantially the entire inner lid surface of the lid.

4. The biological specimen container of claim 1, wherein each of the second ends of the plurality of biasing elements are curled back in a hook shape.

5. The biological specimen container of claim 1, further comprising a deformable porous material formed on the inner bottom surface of the container body.

6. The biological specimen container of claim 1, wherein the container lid is perforated.

7. The biological specimen container of claim 1, wherein the container lid further comprises at least one outward projecting plate configured to display a marked description of the biological specimen.

* * * * *